(12) United States Patent
Wang et al.

(10) Patent No.: US 10,687,755 B2
(45) Date of Patent: Jun. 23, 2020

(54) WEARABLE PHYSIOLOGICAL MONITORING DEVICE

(71) Applicant: MedicusTek Inc., Taipei (TW)

(72) Inventors: Chung-Cheng Wang, Taipei (TW); Chia-Ming Hsu, Taipei (TW); Yu-Chun Hsu, Taipei (TW); Yi-Yuan Chen, Taipei (TW)

(73) Assignee: MedicusTek Inc., Taipei (TW)

( * ) Notice: Subject to any disclaimer, the term of this patent is extended or adjusted under 35 U.S.C. 154(b) by 218 days.

(21) Appl. No.: 15/873,901

(22) Filed: Jan. 18, 2018

(65) Prior Publication Data
US 2018/0325446 A1 Nov. 15, 2018

(30) Foreign Application Priority Data

May 12, 2017 (TW) ............................. 106115826 A (51) Int. Cl.
| | | |
|---|---|---|
| *A61B 5/00* | (2006.01) | |
| *A61B 5/0205* | (2006.01) | |
| *A61B 5/024* | (2006.01) | |
| *A61B 5/107* | (2006.01) | |
| *A61B 5/01* | (2006.01) | |

(52) U.S. Cl.
CPC ........ *A61B 5/4393* (2013.01); *A61B 5/02055* (2013.01); *A61B 5/02405* (2013.01); *A61B 5/02438* (2013.01); *A61B 5/1075* (2013.01); *A61B 5/01* (2013.01); *A61B 5/6804* (2013.01)

(58) Field of Classification Search
CPC .............. A61B 5/4393; A61B 5/02055; A61B 5/02405; A61B 5/02438; A61B 5/1075; A61B 5/01; A61B 5/6804

USPC .......................................................... 600/301
See application file for complete search history.

(56) References Cited

U.S. PATENT DOCUMENTS

| | | | | |
|---|---|---|---|---|
| 4,469,108 A | * | 9/1984 | Goldstein | A61B 5/4393 52/651.11 |
| 5,507,302 A | * | 4/1996 | Barbara | A61B 5/103 600/587 |
| 5,931,783 A | * | 8/1999 | Redano | A61B 5/4393 600/439 |

(Continued)

FOREIGN PATENT DOCUMENTS

| | | |
|---|---|---|
| CN | 104545927 A | 4/2015 |
| CN | 105054942 A | 11/2015 |

(Continued)

*Primary Examiner* — Carl H Layno
*Assistant Examiner* — Michael J Lau
(74) *Attorney, Agent, or Firm* — CKC & Partners Co., LLC (57) ABSTRACT

A wearable physiological monitoring device is provided. The wearable physiological monitoring device includes a wearable object, a sensing module and a processing module. The sensing module is disposed on the wearable object and is configured to stretch based on a local displacement of target organ of the under-test person contacted by the wearable object to generate a change of a sensing value thereof. The processing module is configured to calculate a physiological changing mode that includes physiological information and occurrence time information based on the change of the sensing value. The physiological information includes a number, duration, a degree or a combination of the above of the stretching of the wearable object to determine the health condition of the under-test person.

20 Claims, 6 Drawing Sheets

(56) References Cited

U.S. PATENT DOCUMENTS

| | | | | |
|---|---|---|---|---|
| 6,047,406 A * | 4/2000 | Dicker | A41D 13/0015 | 2/115 |
| 6,050,959 A * | 4/2000 | Card | A61B 5/0533 | 600/587 |
| 6,162,188 A * | 12/2000 | Barnea | A61B 5/4393 | 600/587 |
| 6,814,695 B1 * | 11/2004 | Wyllie | A61B 5/4393 | 600/38 |
| 6,882,897 B1 * | 4/2005 | Fernandez | A41H 3/007 | 700/132 |
| 8,161,826 B1 * | 4/2012 | Taylor | G01L 1/18 | 73/862.044 |
| 2003/0004423 A1 * | 1/2003 | Lavie | A61B 5/1073 | 600/500 |
| 2004/0249299 A1 * | 12/2004 | Cobb | A61B 5/0205 | 600/529 |
| 2009/0183388 A1 * | 7/2009 | Miller | A43B 13/386 | 36/43 |
| 2010/0030117 A1 * | 2/2010 | Li | A61B 5/0059 | 600/587 |
| 2010/0113980 A1 * | 5/2010 | Herr | G01L 5/0061 | 600/587 |
| 2010/0191072 A1 * | 7/2010 | Matsumori | A61B 5/02 | 600/301 |
| 2011/0009713 A1 * | 1/2011 | Feinberg | A61B 5/0205 | 600/301 |
| 2011/0160600 A1 * | 6/2011 | Wu | A61B 5/022 | 600/500 |
| 2011/0295156 A1 * | 12/2011 | Arturi | A61B 5/4393 | 600/587 |
| 2012/0253234 A1 * | 10/2012 | Yang | A61B 5/1038 | 600/595 |
| 2014/0171767 A1 * | 6/2014 | Hotaling | A61B 8/06 | 600/323 |
| 2015/0335288 A1 * | 11/2015 | Toth | A61B 5/6833 | 600/373 |
| 2015/0359457 A1 * | 12/2015 | Blumenthal | A63F 13/50 | 73/172 |
| 2016/0067075 A1 * | 3/2016 | Malinowski | A61F 5/0113 | 602/28 |
| 2016/0081575 A1 * | 3/2016 | Wu | G16H 50/30 | 600/301 |
| 2016/0107309 A1 * | 4/2016 | Walsh | A61H 3/00 | 248/550 |
| 2016/0186366 A1 * | 6/2016 | Mcmaster | D04B 1/14 | 66/202 |
| 2016/0198993 A1 * | 7/2016 | Yuan | A61B 5/6804 | 600/301 |
| 2016/0206010 A1 * | 7/2016 | Lee, III | A41B 9/023 | |
| 2016/0213287 A1 * | 7/2016 | Kuller | A61B 5/091 | |
| 2016/0262685 A1 * | 9/2016 | Wagner | A61B 5/1101 | |
| 2016/0287937 A1 * | 10/2016 | Fitzgerald | G06K 9/00342 | |
| 2017/0036066 A1 * | 2/2017 | Chahine | G16H 40/63 | |
| 2017/0060298 A1 * | 3/2017 | Hwang | G06F 3/04883 | |
| 2017/0079868 A1 * | 3/2017 | Reid, Jr. | A61B 5/0053 | |
| 2017/0105657 A1 * | 4/2017 | Eid | A61B 5/6847 | |
| 2017/0119273 A1 * | 5/2017 | Thakur | A61B 5/4836 | |

FOREIGN PATENT DOCUMENTS

| | | |
|---|---|---|
| CN | 106413452 A | 2/2017 |
| TW | 201143715 A | 12/2011 |
| TW | I483707 B | 5/2015 |
| TW | M505913 U | 8/2015 |

* cited by examiner

WEARABLE PHYSIOLOGICAL MONITORING DEVICE

RELATED APPLICATIONS

This application claims priority to Taiwanese Application Serial Number 106115826, filed May 12, 2017, which is herein incorporated by reference.

BACKGROUND

Field of Invention

The present invention relates to a physiological monitoring technology. More particularly, the present invention relates to a wearable physiological monitoring device.

Description of Related Art

Modern people have more and more concern for the requirement of understanding their physiological status. The requirement for the physiological monitoring device is higher accordingly. Especially, the life in the modern society becomes busier such that it is difficult to free up the time to go to hospital. Further, the diseases of civilization of the modern society become serious to make the requirement for the physiological monitoring device become higher.

There are some common physiological monitoring subjects. For the color Doppler echocardiography, it requires the injection of the vasodilator to the corpus cavernosum penis. Further, the erection function of the patient during the outpatient service is easy to be affected by the echocardiography operated by the doctor and affected by the environment. For the penile angiography, it requires the injection of the photographic developer through the femoral artery, which is invasive and time-consuming. Further, such a technology would expose the patient under the X-ray. For the corpus cavernosography, it requires the injection of the photographic developer to the corpus cavernosum penis, which is also invasive and time-consuming. Further, such a technology would also expose the patient under the X-ray. For the experiment of the penile collar to measure the hardness during night time, it is widely used to distinguish the erection dysfunction caused either cardiogenically or organically. However, it is costly. Further, the accuracy and the reliability of such a technology are not supported by many scientific proofs.

Accordingly, what is needed is a wearable physiological monitoring device to address the above issues.

SUMMARY

The present disclosure provides a wearable physiological monitoring device that includes a wearable object, a sensing module and a processing module. The sensing module is disposed on the wearable object and configured to stretch based on a local displacement of a target organ of an under-test person contacted by the wearable object to generate a change of a sensing value. The processing module is configured to generate a physiological changing mode that comprises physiological information and occurrence time information based on the change of the sensing value sensed by the sensing module, wherein the physiological information comprises a number, a duration, a degree or a combination of the above of the stretching of the wearable object to determine a health condition of the under-test person.

Another aspect of the present disclosure is to provide a wearable physiological monitoring device that includes a wearable object, a sensing module and a processing module. The sensing module is disposed on the wearable object and configured to stretch based on a local displacement of a target organ of an under-test person contacted by the wearable object to generate a first sensing value of a first position of the wearable object and a second sensing value of a second position of the wearable object. The processing module is configured to generate a physiological changing mode that comprises physiological information and occurrence time information based on a change of a sensing value difference between the first sensing value and the second sensing value, wherein the physiological information comprises a number, a duration, a degree or a combination of the above of the stretching of the wearable object to determine a health condition of the under-test person.

These and other features, aspects, and advantages of the present invention will become better understood with reference to the following description and appended claims.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Reference will now be made in detail to the present embodiments of the invention, examples of which are illustrated in the accompanying drawings. Wherever possible, the same reference numbers are used in the drawings and the description to refer to the same or like parts.

Figure 1A:
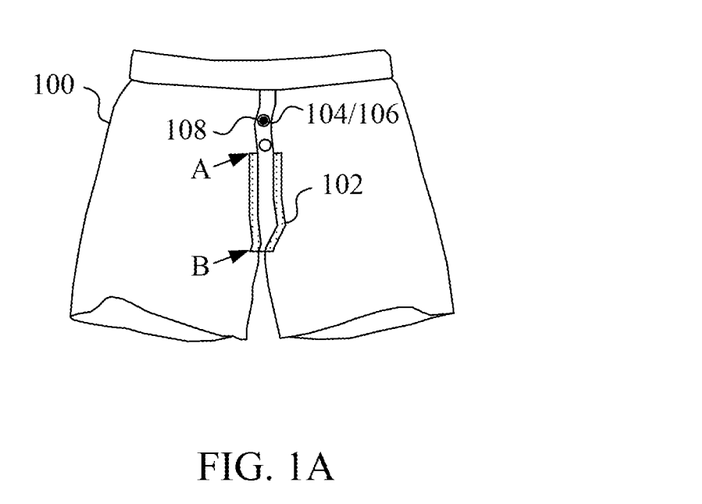
FIG. 1A is a diagram of a wearable physiological monitoring device in an embodiment of the present invention.
Figure 1B:
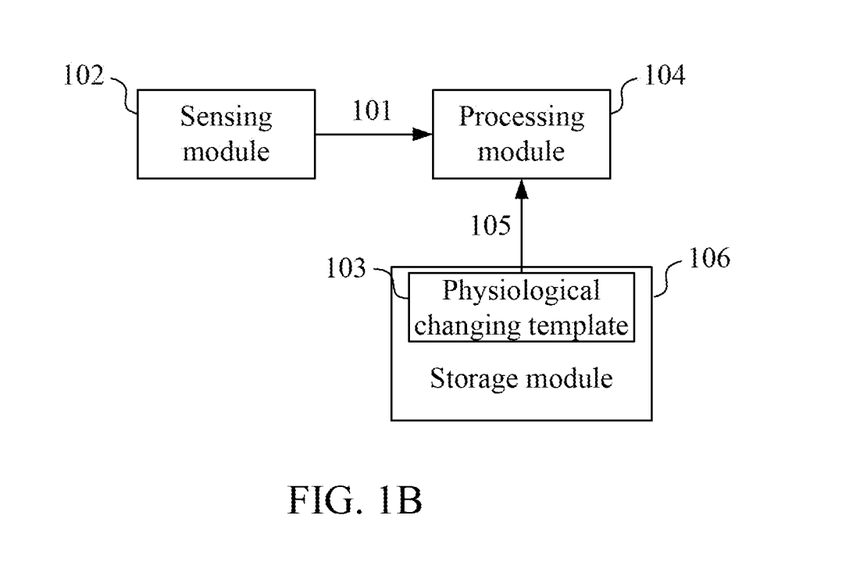
FIG. 1B is a block diagram of the wearable physiological monitoring device in an embodiment of the present invention.

Reference is now made to FIG. 1A and FIG. 1B at the same time. FIG. 1A is a diagram of a wearable physiological monitoring device 1 in an embodiment of the present invention. FIG. 1B is a block diagram of the wearable physiological monitoring device 1 in FIG. 1A in an embodiment of the present invention.

The wearable physiological monitoring device 1 includes a wearable object 100, a sensing module 102, a processing module 104 and a storage module 106. In FIG. 1B, only the information blocks of the wearable physiological monitoring device 1 are illustrated. The wearable object 100 is not illustrated in FIG. 1B.

The wearable object 100 can be worn by an under-test person (not illustrated). In FIG. 1A, an underwear is exemplarily illustrated. In other embodiments, the wearable object 100 can be other kinds of wearable objects depending on the requirements.

The sensing module 102 is disposed on the wearable object 100, such as but not limited to the position having an area filled with dots in FIG. 1A. In an embodiment, the sensing module 102 can be a conductive fiber or a related flexible sensing object. The conductive fiber may include a metal fiber, a carbon fiber, an organic conductive fiber or a combination thereof. In an embodiment, the wearable object 100 includes other flexible fibers besides the sensing module 102. By using textile techniques, the sensing module 102 and the other flexible fibers of the wearable object 100 can be woven to form conductive sensing textiles with high flexibility and high resilience.

In the present embodiment, the sensing module 102 is flexible and is configured to stretch based on a local displacement of a part of an under-test person contacted by the wearable object to generate a change of a resistive value. The part can be target organs such as a wrist, a knee or a waist. For example, when the wearable object 100 is the underwear and the under-test person is male, different degrees of the erection of the penis thereof generate different displacements and result in different degrees of the stretching of the sensing module 102. Different changes of the resistive values are thus generated.

In other embodiments, the sensing module 102 may generate the change of different types of sensing values as well, such as the change of a resistance value, a pressure value, a density value or a capacitance value to accomplish the sensing mechanism.

In the present embodiment, the sensing module 102 includes two strips of conductive fibers disposed at two sides of a penis of the under-test person and substantially vertical to a waist of the under-test person. In other embodiments, the sensing module 102 may include a plurality strips of conductive fibers disposed two sides of a penis of the under-test person in a way similar to FIG. 1A to obtain a larger sensing area.

In the present embodiment, the processing module 104 is electrically coupled to the sensing module 102 and is disposed on the wearable object 100. In an embodiment, when the wearable object 100 is an underwear, the processing module 104 can be disposed at such as, but not limited to a button 108 included by the wearable object 100.

In an embodiment, the processing module 104 is configured to generate a physiological changing mode 101 based on the change of the sensing value sensed by the sensing module 102. In an embodiment, the physiological changing mode 101 includes physiological information and occurrence time information.

The physiological information includes a number, a duration, a degree or a combination of the above of the stretching of the wearable object 100. In an embodiment, the processing module 104 actually senses the change of the current from the sensing module 102 to calculate the number, the duration and degree of the stretching of the wearable object 100 according to the number, the frequency and the intensity of the change of the current.

On the other hand, the occurrence time information corresponds to the occurrence time of the physiological information. The occurrence time may include the duration of the time, the beginning time of the physiological information and the ending time of the physiological information. In an embodiment, the processing module 104 actually senses the time spots of the change of the current from the sensing module 102 to obtain the related time information.

The storage module 106 is configured to store at least one physiological changing template 103. The storage module 106 can be disposed at such as, but not limited to the button 108 included by the wearable object 100. In an embodiment, each of the physiological changing templates 103 include the physiological information and the occurrence time information that correspond to a certain symptom and are obtained according to statistics results. For example, a male person has erection during sleep at night. When the number or the strength of the erection does not reach a certain range of predetermine values during the night, the condition of erectile dysfunction is determined.

As a result, the processing module 104 is further configured to retrieve physiological changing template information 105 from the physiological changing template 103 to compare the physiological changing mode 101 and the physiological changing template information 105 to determine that the under-test person has a symptom when the physiological changing mode 101 matches the physiological changing template information 105.

For example, when the number, the duration, the degree or a combination of the above of the stretching of the wearable object 100 and the occurrence time information match the values of the physiological changing template information 105, the processing module 104 determines that the under-test person that corresponds to the physiological changing mode 101 has a certain symptom.

The embodiment of sensing the erection of the penis of the under-test person is further used herein as an example. The processing module 104 can determine whether the number, the duration and the strength of the erection matches the values of the physiological changing template information 105 according to the number, the duration, the degree or a combination of the above of the stretching of the wearable object 100. Further, the processing module 104 determines whether the occurrence time information matches the values of the physiological changing template information 105 to determine whether the erection function is normal.

As a result, the advantage of the present invention is to use the sensing module 102 to monitor the local displacement of the target organ of an under-test person contacted by the wearable object 100 to generate the change of a sensing value sensed by the sensing module 102 to further generate the physiological changing mode 101. The invasive monitoring method can be avoided. Further, the physiological information can be obtained with a lower cost.

It is appreciated that the processing module 104 can calculate the physiological changing mode 101 according to different sensing methods of the sensing module 102. For example, as illustrated in FIG. 1A, the sensing module 102 is configured to stretch based on a local displacement of a target organ of an under-test person contacted by the wearable object 100 to generate a first resistance value of a first position A of the wearable object 100 and a second resistance value of a second position B of the wearable object 100. The processing module 104 is configured to generate the physiological changing mode 101 based on a change of a sensing value difference between the first sensing value and the second sensing value from the sensing module 102. The processing module 104 further performs the subsequent comparison and determination accordingly.

In an embodiment, the sensing module 102 includes a plurality of sections configured to sense a plurality of resistance values. The processing module 104 determines an extrusion density according to the resistance values to generate three-dimensional sensing values corresponding to the X direction, Y direction and Z direction.

In another embodiment, the processing module 104 of the wearable physiological monitoring device 1 further generates comprehensive determination information according to the physiological changing mode and sensing information generated by other physiological measuring instruments such as, but not limited to a sphygmomanometer, a breathing monitoring device, a blood glucose meter, etc (not illustrated).

Figure 2:
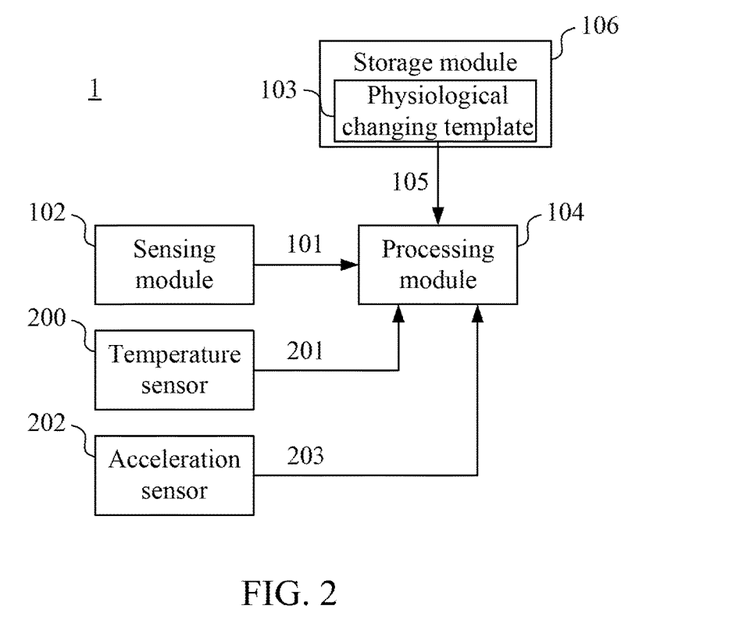
FIG. 2 is a block diagram of the wearable physiological monitoring device in FIG. 1A in another embodiment of the present invention.

Reference is now made to FIG. 2. FIG. 2 is a block diagram of the wearable physiological monitoring device 1 in FIG. 1A in another embodiment of the present invention.

The wearable physiological monitoring device 1 illustrated in FIG. 2 includes the wearable object 100 (not illustrated in FIG. 2), the sensing module 102 and the processing module 104 that have functions identical to the functions of these modules illustrated in FIG. 1B. As a result, the detail of the functions of these modules is not described herein. In the present embodiment, the wearable physiological monitoring device 1 selectively includes a temperature sensor 200 and/or an acceleration sensor 202.

The temperature sensor 200 and the acceleration sensor 202 are disposed on the wearable object 100. In an embodiment, the temperature sensor 200 and the acceleration sensor 202 are disposed at such as, but not limited to other buttons of the wearable object 100.

The temperature sensor 200 is configured to sense temperature information 201 of the wearable object 100. The processing module 104 is configured to determine the change of the temperature of the wearable object 100 according to the temperature information 201. In an embodiment, when the under-test person wets the pants, the urine raises the temperature of the wearable object 100. As a result, by using the temperature information 201 from the temperature sensor 200, the processing module 104 can determine whether the under-test person wets the pants accordingly.

The acceleration sensor 202 is configured to sense displacement amount information 203 of the wearable object 100. The processing module 104 is disposed to determine a change of posture of the under-test person according to the displacement amount information 203. In an embodiment, the processing module 104 determines whether the under-test person is under the sleep status according to the displacement amount information 203 and further determines a reliability of the physiological information 101 corresponding to the occurrence time of the displacement amount information 203.

For example, when the displacement amount of the wearable object 100 is determined to be smaller than a predetermined threshold according to the displacement amount information 203, the processing module 104 determines that the under-test person is under the sleep status and further determines that the physiological information 101 is reliable. On the contrary, when the displacement amount of the wearable object 100 is determined to be larger than or equal to the predetermined threshold according to the displacement amount information 203, the processing module 104 determines that the under-test person is not under the sleep status and further determines that the physiological information 101 is unreliable.

By disposing the temperature sensor 200 and the acceleration sensor 202 mentioned above, the wearable physiological monitoring device 1 can determine the reliability of the physiological changing mode 101 to further improve the accuracy of the sensing.

Figure 3:
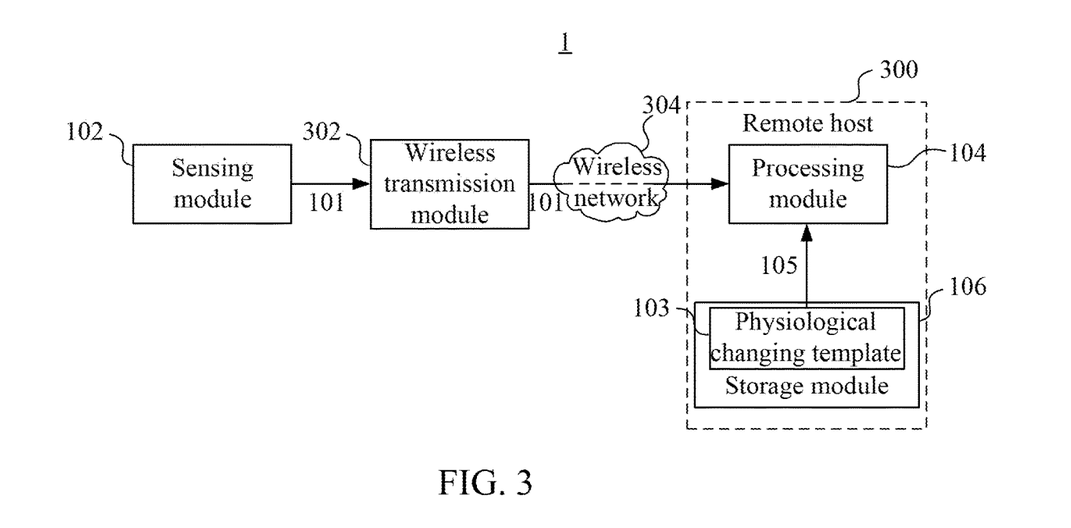
FIG. 3 is a block diagram of the wearable physiological monitoring device in FIG. 1A in yet another embodiment of the present invention.

Reference is now made to FIG. 3. FIG. 3 is a block diagram of the wearable physiological monitoring device 1 in FIG. 1A in yet another embodiment of the present invention.

The wearable physiological monitoring device 1 illustrated in FIG. 3 also includes the wearable object 100 (not illustrated in FIG. 3), the sensing module 102 and the processing module 104 that have functions identical to the functions of these modules illustrated in FIG. 1B. As a result, the detail of the functions of these modules is not described herein. In the present embodiment, the processing module 104 and the storage module 106 are not disposed in a remote host 300 instead of on the wearable object 100. The wearable physiological monitoring device 1 can selectively include a wireless transmission module 302.

The wireless transmission module 302 is disposed on the wearable object 100. In an embodiment, the wireless transmission module 302 is disposed on such as, but not limited to other buttons included by the wearable object 100.

In the present embodiment, the wireless transmission module 302 is configured to transmit the physiological information 101 to the processing module 104 through a wireless network 304 such that the processing module 104 in the remote host 300 processes the physiological information 101.

It is appreciated that the monitoring of the erection function of penis is merely an example of the application. In another embodiment, the wearable object 100 can be implemented by other methods such that the wearable object 100 can be used in different monitoring scenarios.

Figure 4:
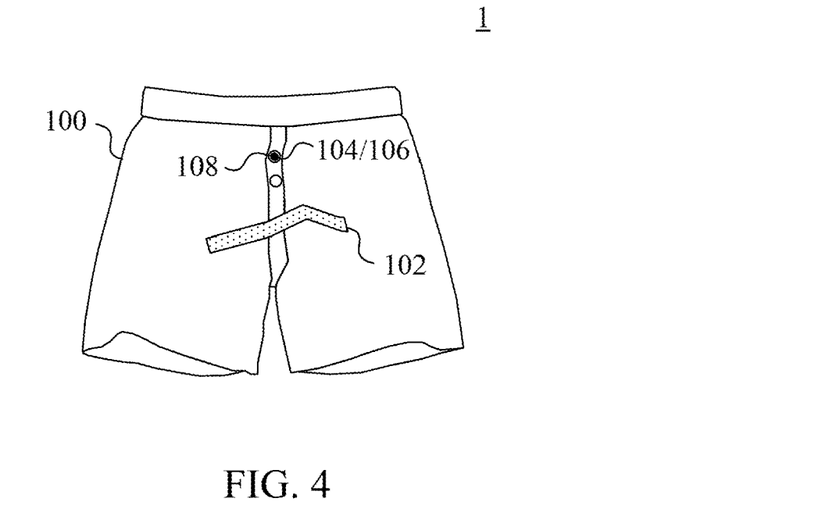
FIG. 4 is a diagram of the wearable physiological monitoring device in another embodiment of the present invention.

Reference is now made to FIG. 4. FIG. 4 is a diagram of the wearable physiological monitoring device 1 in another embodiment of the present invention.

In the present embodiment, the sensing module 102 includes one strip of conductive fiber disposed to correspond to a position of a penis of the under-test person and substantially parallel to a waist of the under-test person. In other embodiments, the sensing module 102 may include a plurality strips of conductive fibers disposed in a way similar to the strip of conductive fiber illustrated in FIG. 4, i.e. substantially parallel to the waist of the under-test person. In other embodiments, the shape of the sensing module 102 can be such as, but not limited to a ring shape corresponding to the penis of the under-test person. A larger range of sensing can be accomplished.

Figure 5:
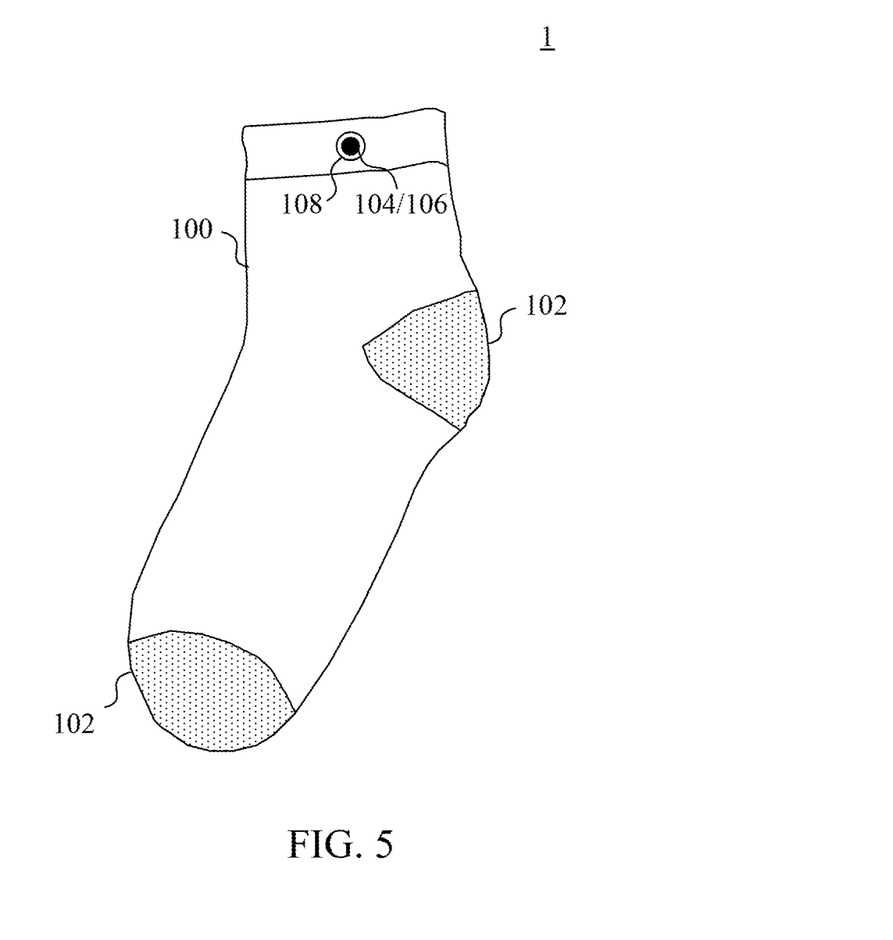
FIG. 5 is a diagram of the wearable physiological monitoring device in another embodiment of the present invention.

Reference is now made to FIG. 5. FIG. 5 is a diagram of the wearable physiological monitoring device 1 in another embodiment of the present invention.

The wearable physiological monitoring device 1 illustrated in FIG. 5 also includes the wearable object 100, the sensing modules 102 and the processing module 104 have functions identical to the functions of these modules illustrated in FIG. 1B. As a result, the detail of the functions of these modules is not described herein.

In the present embodiment, the wearable object 100 is a sock. The number of the sensing modules 102 can be two and each of the sensing modules 102 is disposed at the position having an area filled with dots in FIG. 5. The sensing module 102 is configured to stretch based on a local displacement of the feet of the under-test person to generate a change of a resistance value. The processing module 104 generates the physiological changing mode 101 according to the change of the resistance value to determine whether a gait of the under-test person is normal. The gait includes the frequency, the speed or a combination thereof of the walking of the under-test person.

For example, the processing module 104 can compare the gait sensed from the under-test person with information of predetermined gait, such as the gait of a person having early symptom of Parkinson's disease and the gait of a healthy person. According to the comparison result, whether the gait of the under-test person is normal can be determined to further determine the possibility that the under-test person has the Parkinson's disease.

Figure 6:
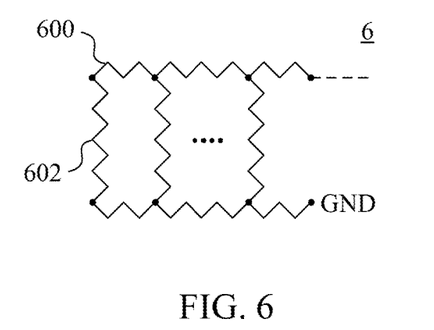
FIG. 6 is a diagram of a sensing unit included in the sensing module in an embodiment of the present invention.

Reference is now made to FIG. 6. FIG. 6 is a diagram of a sensing unit 6 included in the sensing module 102 in an embodiment of the present invention. In the present embodiment, the sensing unit 6 includes two first direction sensing elements 600 and a plurality of second direction sensing elements 602.

One of the first direction sensing elements 600 is electrically coupled to the processing module 104 illustrated in FIG. 1B, and the other one of the first direction sensing elements 600 is electrically coupled to a ground terminal GND. The second direction sensing element 602 is electrically coupled between the two first direction sensing elements 600. The first direction sensing elements 600 stretch along a first direction and the second direction sensing elements 602 stretch along a second direction substantially vertical to the first direction. In an embodiment, the first direction is an X direction and the second direction is a Y direction. In another embodiment, the first direction is the Y direction and the second direction is the X direction.

It is appreciated that in different embodiments, the number of the second direction sensing elements 602 can be one or more that one and is not limited to the number illustrated in FIG. 6.

Figure 7:
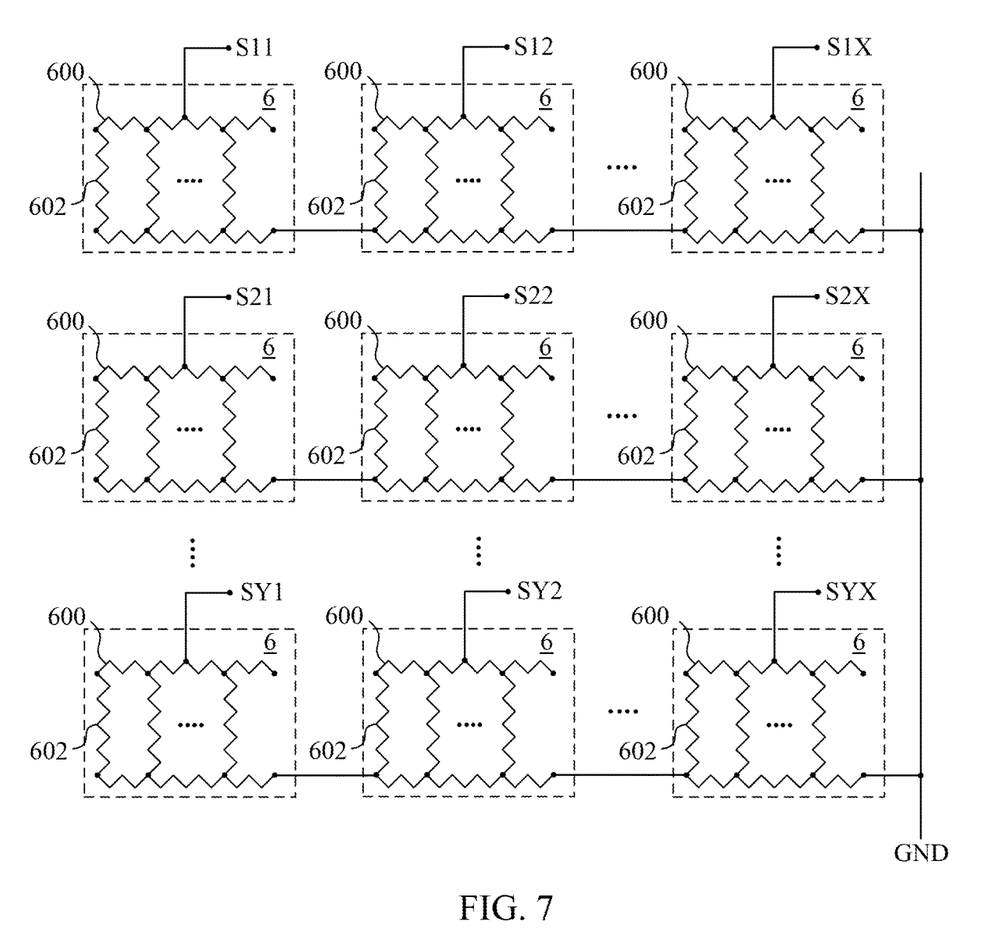
FIG. 7 is a diagram of a plurality of sensing units included in the sensing module in an embodiment of the present invention.

Reference is now made to FIG. 7. FIG. 7 is a diagram of a plurality of sensing units 6 included in the sensing module 102 in an embodiment of the present invention.

Identical to the sensing unit 6 illustrated in FIG. 6, each of the sensing units 6 in FIG. 7 includes two first direction sensing elements 600 and a plurality of second direction sensing elements 602. One of the two first direction sensing elements 600 of each of the sensing units 6 is electrically coupled to the processing module 104 illustrated in FIG. 1 independently through the terminals of S11, S12, . . . , S1X, S21, S22, . . . , S2X, SY1, SY2, . . . and SYX. The other one of the two first direction sensing elements 600 of each of the sensing units 6 is electrically coupled to the ground terminal GND.

It is appreciated that, identical to the sensing unit 6 illustrated in FIG. 6, one of the first direction sensing elements 600 of each of the sensing units 6 in FIG. 7 can stretch along the X direction, and the other one can stretch along the Y direction.

Figure 8A:
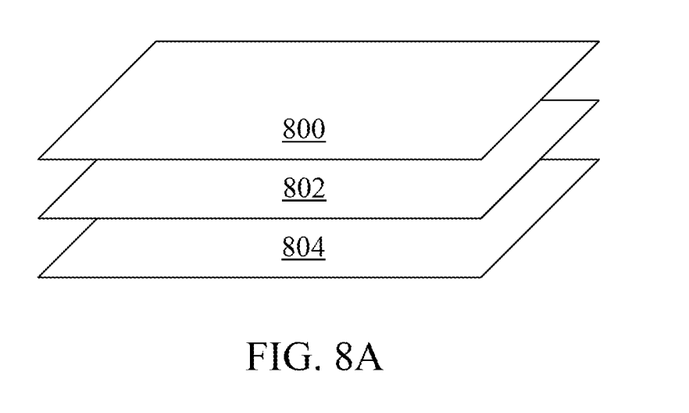
FIG. 8A is a diagram of a first outer layer sensing structure, a central layer sensing structure and a second outer layer sensing structure included in the sensing module in an embodiment of the present invention.
Figure 8B:
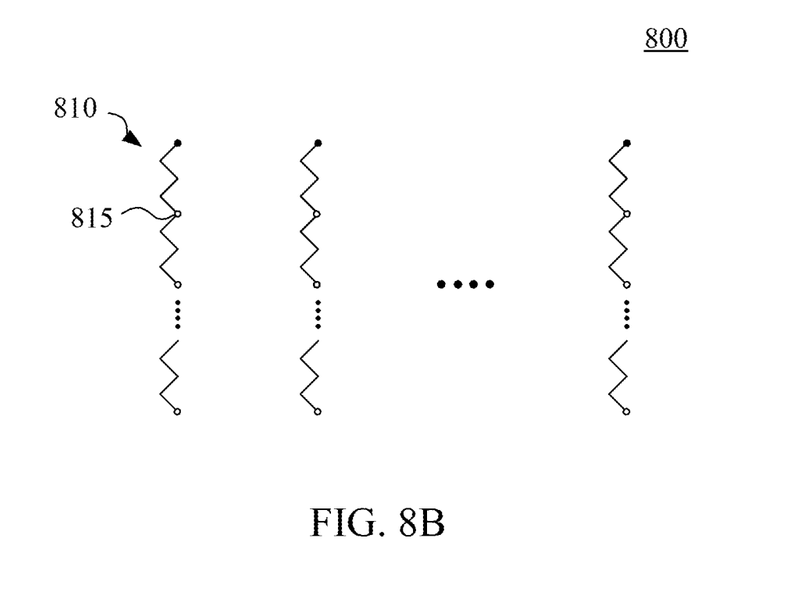
FIG. 8B is a diagram of the first outer layer sensing structure in an embodiment of the present invention.
Figure 8C:
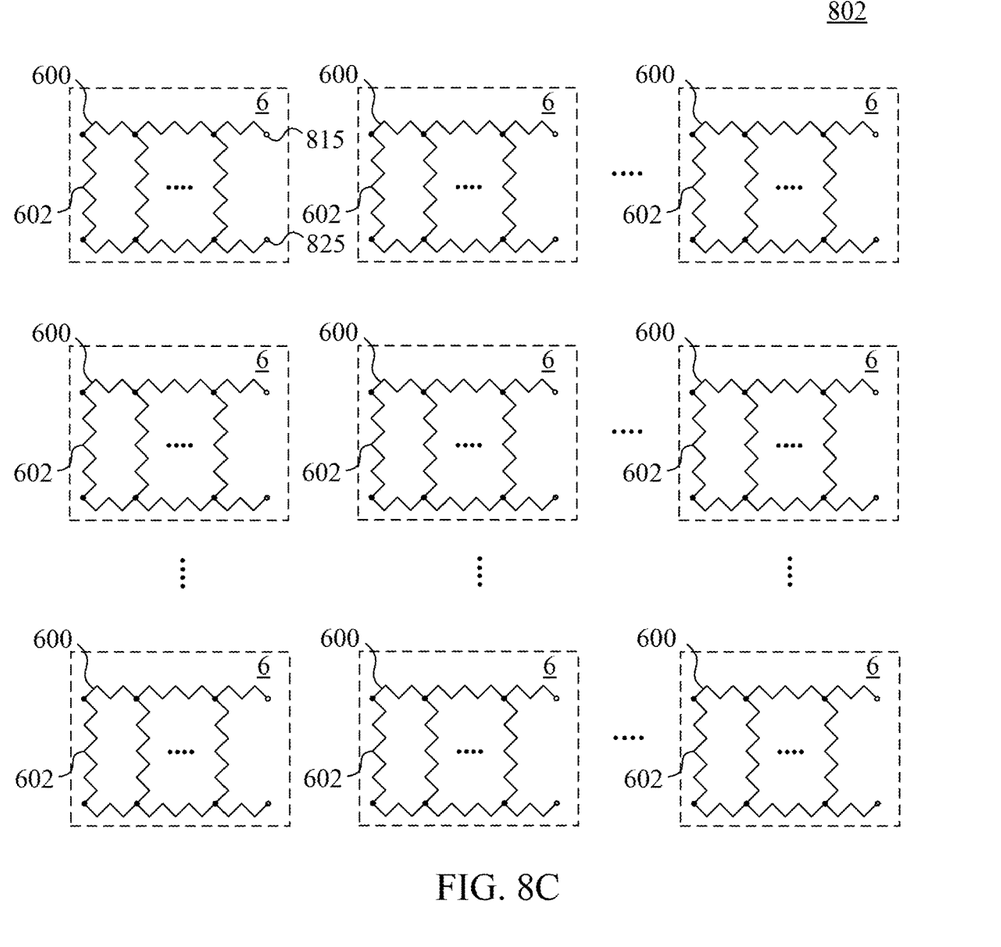
FIG. 8C is a diagram of the central layer sensing structure in an embodiment of the present invention.
Figure 8D:
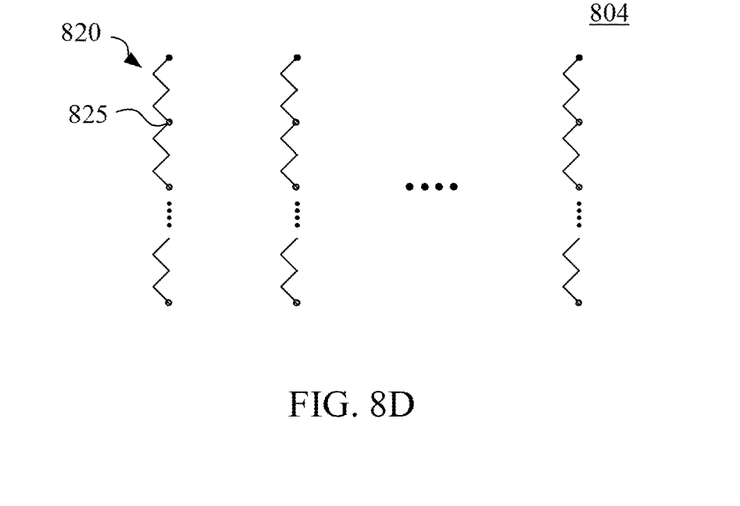
FIG. 8D is a diagram of the second outer layer sensing structure in an embodiment of the present invention.

Reference is now made to FIG. 8A, FIG. 8B, FIG. 8C and FIG. 8D at the same time. FIG. 8A is a diagram of a first outer layer sensing structure 800, a central layer sensing structure 802 and a second outer layer sensing structure 804 included in the sensing module 102 in an embodiment of the present invention. FIG. 8B is a diagram of the first outer layer sensing structure 800 in an embodiment of the present invention. FIG. 8C is a diagram of the central layer sensing structure 802 in an embodiment of the present invention. FIG. 8D is a diagram of the second outer layer sensing structure 804 in an embodiment of the present invention.

The first outer layer sensing structure 800 includes a plurality of second direction sensing structures 810. The central layer sensing structure 802 includes a plurality of sensing units 6 similar to those illustrated in FIG. 7. The second outer layer sensing structure 804 includes a plurality of second direction sensing structures 820.

As a result, in the present embodiment, the second direction sensing structures 810 and the second direction sensing structures 820 stretch in the same direction as the second direction sensing elements 602 of the sensing units 6.

One of the two first direction sensing elements 600 of each of the sensing units 6 is electrically coupled to the processing module 104 illustrated in FIG. 1 through the nodes 815 of the second direction sensing structures 810 of the first outer layer sensing structure 800. The other one of the two first direction sensing elements 600 of each of the sensing units 6 is electrically coupled to the ground terminal GND through the nodes 825 of the second direction sensing structures 820 of the second outer layer sensing structure 804.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A wearable physiological monitoring device comprising:
   a wearable garment;
   a sensing module disposed on the wearable garment and configured to stretch based on a local displacement of a target organ of an under-test person contacted by the wearable garment to generate a change of a sensing value;
   a processing module configured to generate a physiological changing mode that comprises physiological information and occurrence time information based on the change of the sensing value sensed by the sensing module, wherein the physiological information comprises a number, a duration, a degree or a combination of the above of the stretching of the wearable garment to determine a health condition of the under-test person; and a storage module configured to store a plurality of physiological changing templates, wherein each of the physiological changing templates includes physiological information and occurrence time information that correspond to a certain dysfunction symptom, wherein the processing module is further configured to compare the physiological changing mode and the physiological changing templates to determine that the under-test person has a dysfunction symptom when the physiological changing mode matches one of the physiological changing templates.

2. The wearable physiological monitoring device of claim 1, wherein the sensing module is configured to stretch according to a penis displacement of the under-test person, and the processing module determines whether an erection function of the under-test person is normal according to the physiological changing mode.

3. The wearable physiological monitoring device of claim 2, wherein the sensing module at least comprises two strips of sensing elements disposed at two sides of a penis of the under-test person and substantially vertical to a waist of the under-test person.

4. The wearable physiological monitoring device of claim 2, wherein the sensing module at least comprises one strip of sensing element disposed to correspond to a position of a penis of the under-test person and substantially parallel to a waist of the under-test person.

5. The wearable physiological monitoring device of claim 1, further comprising a temperature sensor disposed on the wearable garment and configured to sense temperature information of the wearable garment, and the processing module is configured to determine a temperature change of the wearable garment according to the temperature information.

6. The wearable physiological monitoring device of claim 1, further comprising an acceleration sensor disposed on the wearable garment and configured to sense displacement amount information of the wearable garment, and the processing module is configured to determine a change of posture of the under-test person according to the displacement amount information.

7. The wearable physiological monitoring device of claim 6, wherein the processing module determines a reliability of the physiological information according to the change of posture of the under-test person.

8. The wearable physiological monitoring device of claim 7, wherein the processing module is disposed on a button comprised by the wearable garment.

9. The wearable physiological monitoring device of claim 6, wherein the processing module determines whether the under-test person is under a sleep status according to the change of posture of the under-test person.

10. The wearable physiological monitoring device of claim 1, wherein the sensing module is a conductive fiber comprising a metal fiber, a carbon fiber, an organic conductive fiber or a combination thereof.

11. The wearable physiological monitoring device of claim 1, wherein the processing module is electrically coupled to the sensing module and disposed on the wearable garment.

12. The wearable physiological monitoring device of claim 1, further comprising a wireless transmission module disposed on the wearable garment, and the processing module is disposed in a remote host such that the wireless transmission module is configured to transmit the physiological information to the processing module through a wireless network.

13. The wearable physiological monitoring device of claim 1, wherein the sensing module is disposed to stretch according to a foot displacement of the under-test person, and the processing module determines whether a gait of the under-test person is normal according to the physiological changing mode, wherein the gait comprise a walking frequency, a walking speed and a combination thereof of the under-test person.

14. The wearable physiological monitoring device of claim 1, wherein the sensing module comprises at least one sensing unit that comprises:
two first direction sensing elements, wherein one of the first direction sensing elements is electrically coupled to the processing module, and the other one of the first direction sensing elements is electrically coupled to a ground terminal; and
at least one second direction sensing element electrically coupled between the two first direction sensing elements.

15. The wearable physiological monitoring device of claim 14, wherein the sensing module comprises a plurality of the sensing units, wherein one of the two first direction sensing elements of each of the sensing units is electrically coupled to the processing module independently, the other one of the two first direction sensing elements of each of the sensing units is electrically coupled to the ground terminal.

16. The wearable physiological monitoring device of claim 15, wherein the sensing module comprises:
a first outer layer sensing structure and a second outer layer sensing structure each comprising a plurality of second direction sensing structures;
a central layer sensing structure disposed between the first outer layer sensing structure and the second outer layer sensing structure and comprising a plurality of the sensing units;
wherein one of the two first direction sensing elements of each of the sensing units is electrically coupled to the processing module through the second direction sensing structures of the first outer layer sensing structure, the other one of the two first direction sensing elements of each of the sensing units is electrically coupled to the ground terminal through the second direction sensing structures of the second outer layer sensing structure.

17. The wearable physiological monitoring device of claim 1, wherein the sensing module is further disposed to sense a plurality of the sensing values, and the processing module determines an extrusion density according to the sensing values to generate three-dimensional sensing values.

18. The wearable physiological monitoring device of claim 1, wherein the processing module further generates comprehensive determination information according to the physiological changing mode and sensing information generated by at least one physiological measuring instrument.

19. The wearable physiological monitoring device of claim 1, wherein the sensing value is a value of electric potential, resistance, pressure, density or capacitance.

20. A wearable physiological monitoring device comprising:
a wearable garment;
a sensing module disposed on the wearable garment and configured to stretch based on a local displacement of a target organ of an under-test person contacted by the wearable garment to generate a first sensing value of a first position of the wearable garment and a second sensing value of a second position of the wearable garment;

a processing module configured to generate a physiological changing mode that comprises physiological information and occurrence time information based on a change of a sensing value difference between the first sensing value and the second sensing value, wherein the physiological information comprises a number, a duration, a degree or a combination of the above of the stretching of the wearable garment to determine a health condition of the under-test person; and a storage module configured to store a plurality of physiological changing templates, wherein each of the physiological changing templates includes physiological information and occurrence time information that correspond to a certain dysfunction symptom, wherein the processing module is further configured to compare the physiological changing mode and the physiological changing templates to determine that the under-test person has a dysfunction symptom when the physiological changing mode matches one of the physiological changing templates.

* * * * *